US009629915B2

(12) United States Patent
Pilgaonkar et al.

(10) Patent No.: US 9,629,915 B2
(45) Date of Patent: *Apr. 25, 2017

(54) SUSTAINED RELEASE DOSAGE FORM

(71) Applicant: Rubicon Research Pvt. Ltd., Mumbia (IN)

(72) Inventors: Pratibha S Pilgaonkar, Mumbai (IN); Maharukh T Rustomjee, Mumbai (IN); Anilkumar S Gandhi, Mumbai (IN); Paras R Jain, Mumbai (IN); Atul A Kelkar, Mumbai (IN)

(73) Assignee: Rubicon Research Private Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/562,091

(22) Filed: Dec. 5, 2014

(65) Prior Publication Data

US 2015/0150991 A1    Jun. 4, 2015

Related U.S. Application Data

(63) Continuation of application No. 11/994,385, filed as application No. PCT/IN2006/000230 on Jul. 3, 2006, now Pat. No. 8,920,837.

(51) Int. Cl.
*A61K 9/20*       (2006.01)
*A61K 31/135*    (2006.01)
(Continued)

(52) U.S. Cl.
CPC ............ *A61K 47/38* (2013.01); *A61K 9/2013* (2013.01); *A61K 9/2027* (2013.01); *A61K 9/2054* (2013.01); *A61K 31/135* (2013.01); *A61K 31/138* (2013.01); *A61K 31/155* (2013.01); *A61K 31/194* (2013.01);
(Continued)

(58) Field of Classification Search
CPC .. A61K 31/135; A61K 31/138; A61K 31/155; A61K 31/194; A61K 31/277; A61K 31/375; A61K 31/404; A61K 31/4458; A61K 47/10; A61K 47/12; A61K 47/14;
(Continued)

(56) References Cited

U.S. PATENT DOCUMENTS 3,456,049 A    7/1969   Hotko et al.
4,792,452 A    12/1988   Howard et al.
(Continued)

FOREIGN PATENT DOCUMENTS

EP         0682945       11/1995
EP         1138321       3/2001
(Continued)

OTHER PUBLICATIONS

Ruchatz et al. (KOLLIDON® SR product sheet, Apr. 2000, pp. 1-2).*

(Continued)

*Primary Examiner* — Aradhana Sasan
(74) *Attorney, Agent, or Firm* — Baker Donelson; Nigamnarayan Acharya

(57) ABSTRACT

The novel sustained release dosage form comprising an active agent and a combination of a non-swelling pH dependent release retardant and a non swelling pH independent release retardant polymer which provides pH-independent drug release for a considerable period of time after administration.

20 Claims, 5 Drawing Sheets

(51) Int. Cl.
*A61K 31/138* (2006.01)
*A61K 31/155* (2006.01)
*A61K 31/194* (2006.01)
*A61K 31/277* (2006.01)
*A61K 31/375* (2006.01)
*A61K 31/404* (2006.01)
*A61K 31/4458* (2006.01)
*A61K 47/10* (2006.01)
*A61K 47/12* (2006.01)
*A61K 47/14* (2006.01)
*A61K 47/38* (2006.01)
*A61K 47/32* (2006.01)

(52) U.S. Cl.
CPC .......... *A61K 31/277* (2013.01); *A61K 31/375* (2013.01); *A61K 31/404* (2013.01); *A61K 31/4458* (2013.01); *A61K 47/10* (2013.01); *A61K 47/12* (2013.01); *A61K 47/14* (2013.01); *A61K 47/32* (2013.01)

(58) Field of Classification Search
CPC ...... A61K 47/32; A61K 47/38; A61K 9/2013; A61K 9/02; A61K 9/2054
See application file for complete search history.

(56) References Cited

U.S. PATENT DOCUMENTS

| | | | |
|---|---|---|---|
| 4,927,640 A | 5/1990 | Dahlinder et al. | |
| 4,957,745 A | 9/1990 | Jonsson et al. | |
| 5,246,714 A | 9/1993 | Dahlinder et al. | |
| 6,251,430 B1 * | 6/2001 | Zhang | A61K 9/2027 424/464 |
| 6,346,268 B1 | 2/2002 | Zhang et al. | |
| 8,920,837 B2 * | 12/2014 | Pilgaonkar et al. | 424/468 |
| 2004/0009220 A1 | 1/2004 | Sharma | |
| 2006/0182797 A1 * | 8/2006 | Karavas et al. | 424/456 |
| 2006/0280795 A1 * | 12/2006 | Penhasi et al. | 424/472 |

FOREIGN PATENT DOCUMENTS

| | | |
|---|---|---|
| WO | 97/45091 | 12/1997 |
| WO | 00/45793 | 8/2000 |
| WO | 02/058676 | 8/2002 |
| WO | 2004/054568 | 7/2004 |
| WO | 2005/013960 | 2/2005 |
| WO | 2005/039481 | 5/2005 |

OTHER PUBLICATIONS

PCT International Search Report for PCT/IN2006/000230, May 7, 2007.
Kollidon(R) SR Technical Information, BASF, EMP 030728e-07, Jun. 2008.
"Kollidon(R) VA 64 Fine" Technical Information, BASF, EMP 050602e-05, Jun. 2008.

* cited by examiner

SUSTAINED RELEASE DOSAGE FORM

FIELD OF INVENTION

The present invention relates to a novel sustained release dosage form of an active agent comprising a combination of a non-swelling pH dependent release retardant and a non swelling pH independent release retardant and providing pH-independent drug release for a considerable period of time after administration.

The present invention particularly relates to active agents having solubility of greater than 1 mg/ml.

BACKGROUND OF INVENTION

The advantages of sustained release formulations are well known in the pharmaceutical field. These include the ability of the given pharmaceutical preparation to maintain a desired therapeutic effect over a comparatively longer period of time, reduced side effects, etc. Moreover, for drugs having a short elimination half-life, less frequent administration and better patient compliance may be obtained with sustained release preparations as compared to the conventional dosage forms.

Development of a sustained release dosage form demands considerable understanding of the gastrointestinal physiology. There is a natural pH gradient down the gut from acidity of stomach to weakly acidic duodenum to the neutral environment of the small intestine. Also there are possible fluctuations in pH arising from dietary changes.

Another important factor is the transit time of the dosage form. Transit time determines the time period for which a dosage form remains in a particular segment of gastrointestinal tract. The transit time usually depends on the dosage form itself, gastric motility, presence of food etc.

Combination of pH and transit time determines the environment experienced by a dosage form for example transit time of a tablet in stomach under fasting condition may range from 0.5-2 hours. This means that a tablet will experience a pH of less than 2 for a period of 0.5-2 hours.

These factors, i.e. transit time and pH are highly variable for different individuals, same individual at different time periods, and therefore these factors become very crucial for release of active agent particularly from a modified release dosage form. It is always desirable for optimal use of the drug product that the product be independent of these variabilities and avoid the associated problems of bioavailability variation.

Prior art discloses many patents on controlled and sustained release delivery systems, some of which also describes formulations giving pH independent release profiles.

U.S. Pat. Nos. 4,927,640, 4,957,745 and 5,246,714 describe controlled release beads comprising a compact inert core, which is insoluble and a polymeric membrane. The inner core is made of silicon dioxide, glass or plastic resin particles while the polymeric membrane covering the pharmaceutically active compound may be ethyl cellulose, hydroxypropyl cellulose, hydroxypropyl methylcellulose, hydroxypropyl methyl phthalate, cellulose acetate phthalate, Eudragit RL or Eudragit RS. Although such systems provide pH independent release profile, the process of manufacturing is very complicated and involves use of organic solvents, which is not desirable. The complicated manufacturing steps make the process cumbersome, time consuming and expensive.

U.S. Pat. No. 4,792,452 discloses controlled release pharmaceutical compositions, which provide pH-independent release for a basic drug. The formulations include a pH-dependent polymer, which is a salt of alginic acid, a pH-independent hydrocolloid gelling agent and a binder and the formulation is free of calcium ion and carbon dioxide-producing material. The salt of the alginic acid is preferably sodium alginate or potassium alginate. This patent is applicable only for basic drugs and cannot be applied to acidic or neutral drugs. Moreover the system is dependent on highly variable physiological conditions for conversion of sodium alginate to alginic acid and back to sodium alginate. This may result in inter patient as well as intra patient variabilities leading to suboptimal product performance.

WO02058676 describes a composition exhibiting a pH independent release profile of an active having pH dependent solubility. The formulation comprises a combination of pH independent and a pH dependent polymer which increases dissolution rate of active at a pH greater than 5.5.

WO0045793 discloses extended release formulations of acidic drugs, which have reduced dependence of release rate on pH. The dosage form includes a neutral water swellable hydrophilic polymer and acid soluble polymer, which is water swellable above pH 5.0.

U.S. Pat. No. 6,346,268 discloses a controlled release formulation comprising a pH dependent gelling polymer, an enteric polymer and a pH independent gelling polymer.

The last three patents, mentioned above, describe formulations of drugs having pH dependent solubilities, which tend to make the release of drug also pH dependent. These patents therefore employ a pH dependent polymer to increase the dissolution of the drug in a medium, where its solubility is low, so as to achieve constant drug release. These patents also disclose use of a pH independent, swelling release-retarding polymer, which control the release of the active agent. These systems however may not be useful for drug molecules having high aqueous solubility, which is independent of the pH of the medium. Use of these systems may result in undesirably high initial burst release of the drug.

Thus there is a need to develop a sustained release dosage form, which performs reproducibly with low variability. Such dosage forms would have two essential features—(1) pH independent drug release for a considerable period of time and, (2) absence of significant swelling of the dosage form leading to predictable gastrointestinal transit profile.

It was surprisingly found that both these desired features were achieved by the dosage form of the present invention by employing a combination of a non-swelling pH dependent release retardant and a non-swelling pH independent release retardant. It is generally known in the art that use of pH dependent release retardants alone results in a release profile of the active ingredient, which is dependent on the pH of the environment. However optimal selection of type and concentration of release retardants by the present inventors has resulted in a sustained release dosage form, which releases drug at a rate that is independent of the surrounding milieu for a considerable period of time.

OBJECT OF INVENTION

It is an object of the present invention to provide oral sustained release dosage forms of pharmaceutically active agents comprising a combination of non-swelling pH dependent release retardant and non-swelling pH independent release retardant.

It is a further object of the present invention to provide an oral sustained release dosage form for drugs having aqueous solubility of at least 1 mg/ml.

It is another object of the invention to provide a pH independent drug release profile for a considerable period of time after administration of the dosage form.

Yet another object of the present invention is to provide a method for preparation of sustained release dosage form, wherein the non-swelling pH dependent release retardant and the non-swelling pH independent release retardant are added intragranularly or extragranularly or both such that pH independent drug release is obtained for a considerable period of time after administration.

Yet another further object of the present invention is to provide an oral sustained release dosage form.

SUMMARY OF INVENTION

According to a broad aspect of the present invention there is provided an oral sustained release dosage form comprising,
- (i) therapeutically effective amount of pharmacologically active ingredient having aqueous solubility of greater than 1 mg/ml,
- (ii) at least one non-swelling pH dependent, release retardant, and
- (iii) at least one non-swelling pH independent, release-retardant, wherein the said dosage form provides pH independent drug release for a considerable period of time after administration.

DESCRIPTION OF INVENTION

Figure 1:
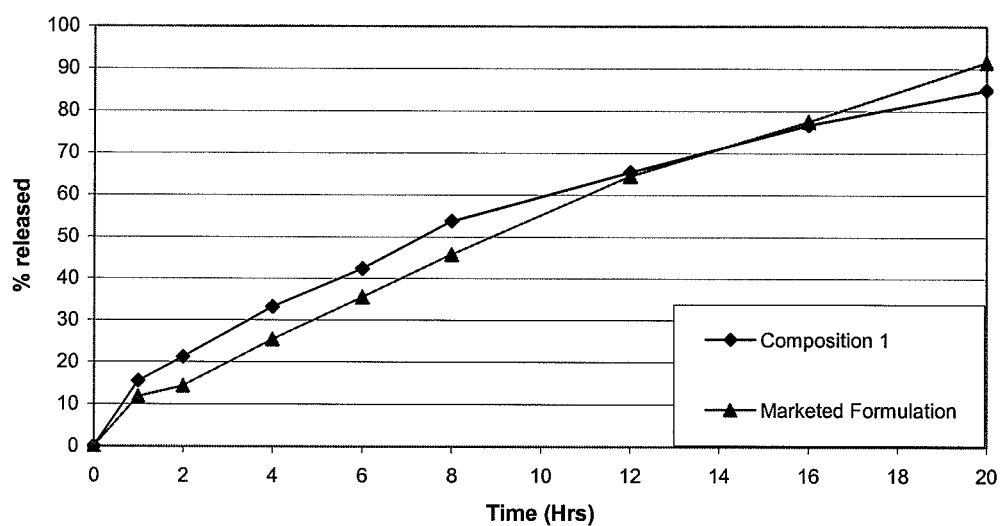
FIG. 1: In vitro release of composition 1 in pH 6.8 phosphate buffer.

The present inventors have addressed the need of developing a sustained release dosage form providing pH independent drug release profile. It was surprisingly found that the much desired pH independent drug release was achieved using a combination of pH dependent release retardant and pH independent release retardant. Also the use of non-swelling release retardants maintains the size of the dosage form thus avoiding variability of drug release rates arising from variable transit times of the dosage form through the gastrointestinal tract.

The term 'non-swelling' as used here includes any excipient that does not swell in water or swells only moderately. This definition does not include excipients such as super disintegrants and polymers such as polyethylene oxide that swell voluminously in contact with water or aqueous media.

The term 'release retardant' as used here means any excipient that can retard the release of an active pharmaceutical ingredient and includes polymers, waxes, fatty acids etc.

A pH dependent release retardant is the one, which has pH dependent solubility, and hence its performance depends on the pH of the environment it encounters.

A pH independent release retardant is the one whose solubility is independent of pH and hence its performance does not depend on the pH of the environment it encounters.

'Considerable period of time' as per this invention means the period equivalent to the normal residence time of the dosage form in the stomach i.e. up to 2-6 hours.

The Active Agent

The present invention provides a sustained release formulation of a pharmacologically active agent having an aqueous solubility of greater that 1 mg/ml and may be acidic, basic or neutral in character. The invention is also applicable to active agents at different dose levels and variable solubility. The active agents may be selected from one of the following therapeutic classes that include:

anti-inflammatory, antipyretic, anticonvulsant and/or analgesic agents, tuberculostats, cardiocirculatory system drugs, antihistaminic agents, hypnotic sedatives, antineoplastic agents, antineoplastic agents, antineoplastic agents, bronchodilators, antiarrhythmic agents, surface anesthetics, antiepileptic, synthetic adrenocortical steroids, digestive system drugs or antibiotics.

The active agents may be selected from Neomycin Sulphate, Verapamil hydrochloride, Brimonidine tartrate, Morphine Sulphate, Lamivudine, Mepivacaine hydrochloride, Zidovudine, Lisinopril, Ropinirole hydrochloride, Abacavir sulphate, Pentoxifylline, valcyclovir hydrochloride, Albuterol Sulphate, Daunorubicin, Ranitidine hydrochloride, Clonidine hydrochloride, Ondansetron hydrochloride, Diltiazem hydrochloride, Acyclovir Sodium, Albuterol Sulphate, Pravastatin Sodium, Didanosine, Atenolol, Stavudine, Mesalazine Sodium, Zanamirin, Doxycycline hyclate, Donepezil hydrochloride, Methyldopa, Timolol maleate, Naloxone hydrochloride, Alendronate sodium, Rizatriptan beuzoate, Mecamylamine hydrochloride, Phenoxybenzamine hydrochloride, Captopril, Fluvastatin sodium, Benazepril hydrochloride, Alburerol Sulphate, Pentosan polysulphate sodium, Levofloxacin, Cetirizine hydrochloride, Clidaymycin phosphate, Warfarin sodium, Propoxyphene hydrochloride, Potassium chloride, Pramipexole hydrochloride, Metoprolol succinate, Metoprolol tartrate, Metformin hydrochloride, Losartan potassium, Methyl phenidate hydrochloride, Montelukast sodium, Bisoprolol fumarate, Oxymorphoine hydrochloride, Amantadine hydrochloride, Sumatriptan succinate, Tramadol hydrochloride, Phenobarbital sodium, Cimetidine hydrochloride, Quinapril hydrochloride, Levomisole hydrochloride, Gabapentin, Ampicillin hydrochloride, Ceftrioxone sodium, Mepiridine hydrochloride, Guanidine hydrochloride, Venlafaxine hydrochloride, Propranolol hydrochloride, Promethazine hydrochloride, Bupropion hydrochloride, Phenylephrine hydrochloride, Ascorbic acid and so on.

In the embodiments of the invention, the active agent can be present in any suitable form. For example, it can be in the form of a particle, powder, a crystal, or a granule.

In certain embodiments of the present invention, one or a combination of more than one active ingredients can also be employed.

Amount of active ingredient employed in the dosage form will be generally dependent on the therapeutically effective amount of the active ingredient. However the amount of active ingredient present in the dosage form can range from 1-80%, preferably 5-50% and more preferably 10-40% by weight of the dosage form Non-Swelling pH Dependent Release Retardants.

These are the excipients whose performance is dependent on the pH of the medium. A number of such excipients known in the art include poly methacrylic acid derivatives, cellulose derivatives, acrylic acid derivatives, maleic acid copolymers, polyvinyl derivatives etc.

Cellulose based pH dependent release retardant include hydroxypropylmethylcellulose acetate succinate, hydroxypropylmethylcellulose phthalate, hydroxymethylethylcellulose phthalate, cellulose acetate phthalate, cellulose acetate succinate, cellulose acetate maleate, cellulose acetate trimelliate cellulose benzoate phthalate, cellulose propionate phthalate, methylcellulose phthalate, carboxymethylethylcellulose, ethylhydroxyethylcellulose phthalate and the like.

Acrylic copolymer based pH dependent release retardant include styrene•acrylic acid copolymer, methyl acrylate acrylic acid copolymer, methyl acrylate•methacrylic acid copolymer, butyl acrylate•styrene•acrylic acid copolymer, methacrylic acid•methyl methacrylate copolymer (e.g. Trade-names: Eudragit L 100 and Eudragit S, available from Röhm Pharma), methacrylic acid•ethyl acrylate copolymer (e.g. Trade-name: Eudragit L 100-55, available from Röhm Pharma), methyl acrylate•methacrylic acid•octyl acrylate copolymer Maleic copolymer based pH dependent release retardant include vinylacetate•maleic acid anhydride copolymer, styrene•maleic acid anhydride copolymer, styrene•maleic acid monoester copolymer, vinylmethylether maleic acid anhydride copolymer, ethylene•maleic acid anhydride copolymer, vinylbutylether•maleic acid anhydride copolymer, acrylonitrile methyl acrylate•maleic acid anhydride copolymer, butyl acrylate•styrene•maleic acid anhydride copolymer and the like.

Polyvinyl derivative based pH dependent release retardant includes polyvinyl alcohol phthalate, polyvinylacetal phthalate, polyvinyl butylate phthalate, polyvinylacetoacetal phthalate and the like.

Among these examples, methacrylic acid•methylmethacrylate copolymer and methacrylic acid•ethylacrylate copolymer are preferable which are available under the brand name Eudragit®.

Eudragit is the trade name for a number of film coating substances on an acrylic resin basis produced by Rohm Pharma. Eudragit L100® is used in matrix sustained release formulations especially for reducing burst release (excessive drug release in initial hours) by reducing the extent of water penetration in the initial hours as eudragit L100® is hydrophobic in nature and it causes poor wettability of the tablet surface. However, Eudragit L100® shows pH dependent solubility in aqueous media; insoluble in acidic media but soluble from pH 6.0, which results in a pH dependent drug release profile (which means slower release in acidic media and faster release in alkaline media). This pH dependent behavior poses major limitation on the use of Eudragit L100® as sustained release matrix forming agent especially when pH independent drug release is desired. Examples of other pH dependent polymers belonging to class of polymethacrylates that can be used in the present invention are provided in Table 1.

TABLE 1 pH dependent polymers of polymethacrylates class

| Generic name | Brand names | Marketed by |
| --- | --- | --- |
| Poly (methacrylic acid, methyl methacrylate) 1:1 | Eudragit L 100 | Röhm GmbH |
| | Eudragit L 12.5 | Röhm GmbH |
| | Eudragit L 12.5 P | Röhm GmbH |
| | Eudragit L 30 D-55 | Röhm GmbH |
| Poly (methacrylic acid, ethyl acrylate) 1:1 | Eudragit L 100-55 | Röhm GmbH |
| | Eastacryl 30D | Eastman Chemical |
| | Kollicoat MAE 30 D | BASF Fine Chemicals |
| | Kollicoat MAE 30 DP | BASF Fine Chemicals |
| Poly (methacrylic acid, methyl methacrylate) 1:2 | Eudragit S 100 | Röhm GmbH |
| | Eudragit S 12.5 | Röhm GmbH |
| | Eudragit S 12.5 P | Röhm GmbH |

The pH dependent release retardant may be included in the formulation at 10-90% by weight, preferably 15-75% and more preferably 20-50% by weight of the dosage form.

Non-Swelling pH Independent Release Retardants

These are the excipients whose performance is independent of the pH of the environment. Many of these are hydrophilic and swell in aqueous environment. Such release retardants due to their swelling/gelling nature, may cause variability of drug release and absorption due to food effect, adhesion to the mucosa, retention in stomach etc. Therefore in order to reduce variabilities associated with such swelling excipients, the present invention employs only non-swelling release retardants.

Non-swelling pH independent release retardants may be selected from excipients that include polyvinyl alcohol, polyvinyl acetate, Kollidon SR (which is a mixture of 8 parts w/w of polyvinyl acetate and 2 parts w/w of polyvinylpyrrolidone, Polymethacrylic acid derivatives, cellulose derivatives such as ethyl cellulose, triglycerides, waxes such as compritol, lubritab, peceol, gelucires, lipids, fatty acids or their salts or derivatives such as stearic acid, etc. Kollidon SR is the most preferred release retardant.

Kollidon SR is a sustained release matrix forming agent consisting of polyvinyl acetate (8 parts w/w) and polyvinylpyrrolidone (2 parts w/w). It has free-flowing, non-hygroscopic and direct compressibility properties (high dry binding capacity). Further, in vitro drug release profiles of tablet formulations with Kollidon SR as sustained release matrix forming agent are not influenced by the compression force used, pH and ionic strength of the dissolution media, and speed of agitation. This unique property of Kollidon SR makes it one of the most promising sustained release matrix forming agents especially where pH independent drug release is desired. However Kollidon SR based formulations have tendency to show higher burst release (excessive drug release in initial hours) by dissolution of drug remaining on the tablet surface as soon as the tablet comes in contact with aqueous media/fluid. This tendency can lead to deviation of the drug release kinetics far away from the intended zero order kinetics (linear release). Thus, higher burst release poses a major limitation to the use of Kollidon SR as sustained release matrix forming agent when initial burst release is to be avoided.

The pH independent release retardant may be included in the formulation at 10-90% by weight concentration, preferably 15-75% and more preferably 20-50% by weight According to a preferred aspect of the present invention, it was surprisingly found that a combination of a pH dependent release retardant (e.g. Eudragit L100®) and a pH independent release retardant (e.g. Kolidon SR) provides pH independent drug release profile along with minimal initial burst release of the drug.

The formulation is easy to scale up as it involves processes routinely carried out in pharmaceutical industry. As the formulation is minimally affected by physiological variations, low patient-to-patient variability is to be expected.

The controlled release dosage forms according to the present invention can be in the form of tablets, capsules, pellets, granules, powders etc.

When the dosage form is in the form of tablets, additional excipients conventionally known in art such as filler, binders and lubricants may be incorporated. Fillers such as lactose monohydrate, microcrystalline cellulose, dicalcium phosphate may be used, The binders are selected from the group comprising of starch, polyethylene glycol, polyvinylpyrrolidone, hydroxypropyl methyl cellulose and hydroxypropylcellulose and natural and synthetic gums. Lubricants like Aerosil-200, Magnesium stearate and hydrogenated vegetable oils or triglycerides of stearic acid, palmitic acid may be utilized.

The said dosage form as per present invention can be prepared by dry granulation or direct compression or wet granulation techniques, usually employed in the industry.

In one of the embodiments of the present invention, the composition may optionally be coated. Surface coating may be employed for aesthetic purposes or for dimensionally stabilizing the compressed tablet. The coating may be carried out using any conventional technique employing conventional ingredients suitable for enteral use. A surface coating can for example be in the form of film using conventional polymers such as hydroxypropyl methyl cellulose, hydroxypropyl cellulose, carboxymethyl cellulose, polyvinyl alcohol poly methacrylates and the like.

In another embodiment of the present invention, the composition may optionally be coated with a functional coat. The coat can be employed using hydrophilic polymers, hydrophobic polymers, waxes etc. either alone or in combination, along with plasticizers, colorants, opacifiers etc. The functional coat may provide a further reduction in initial burst release to achieve a near zero order drug release profile. The functional coat may also inhibit the release of active ingredient in the stomach, if so desired.

In a further illustrative embodiment, a solid pharmaceutical composition may be in the form of a multilayer system for oral administration. The system may be adapted to deliver two different active agents.

In a further illustrative embodiment a solid pharmaceutical composition in the form of a multilayer system for oral administration is adapted to deliver an active pharmaceutical agent from a first layer immediately upon reaching the gastrointestinal tract, and to deliver a further pharmaceutical agent which may be same or different from a second layer, in a controlled manner over a specific time period.

While the present invention has been described in terms of its specific embodiments, certain modifications and equivalents will be apparent to those skilled in the art and are intended to be included within the scope of the present invention.

The details of the invention, its objects and advantages are explained hereunder in greater detail in relation to non-limiting exemplary illustrations.

EXAMPLES

Example 1

Preparation and the Drug Release Profile of the Sustained Release Tablet Dosage Form This example provides pH independent drug release by formulating a matrix tablet of metoprolol, comprising a pH dependent release from a retarding polymer (Eudragit L100®) and a pH independent release-retarding polymer (Kolidon SR).

TABLE 2

Composition of the formulation

| Ingredients | Composition 1 (mg/tablet) |
| --- | --- |
| Metoprolol succinate | 47.5 |
| Poly (methacrylic acid, methyl methacrylate) (Eudragit L100 ®) | 80 |
| Copovidone (Kollidon VA 64) | 10 |
| Kolidon SR | 70 |
| Magnesium stearate | 2.5 |
| Water, Purified | q.s. |

Procedure

Weighed quantities of metoprolol succinate and Eudragit L100® were granulated using solution of Kollidon VA 64 in water. Granules were mixed with Kolidon SR and magnesium stearate and then compressed on a tablet machine.

In vitro drug release was studied in 500 ml of pH 6.8 buffer using USP type II dissolution apparatus with 50 rpm rotation speed and temperature being 37±1° C.

Table 3 shows the drug release profile of composition 1 in comparison with the commercial product of metoprolol succinate tablet dosage form.

TABLE 3

In vitro drug release in pH 6.8 buffer

| Time (hrs) | Composition 1 % Cumulative Drug Release | A Marketed product % Cumulative Drug Release |
| --- | --- | --- |
| 0 | 0 | 0 |
| 1 | 15.5 | 11.87 |
| 2 | 21.2 | 14.34 |
| 4 | 33.2 | 25.43 |
| 6 | 42.3 | 35.50 |
| 8 | 53.7 | 45.75 |
| 12 | 65.4 | 64.46 |
| 16 | 76.6 | 77.44 |
| 20 | 84.9 | 91.5 |

As evident from the above table and FIG. 1, composition 1 provides a release profile that is similar to the marketed formulation in pH 6.8 medium.

Example 2 pH Independent Release Profile

To determine the pH independent release behavior in vitro dissolution of composition 1 was carried out in 0.1N HCl. The dosage form is expected to be retained in stomach for a period of 2-4 hours under different physiological conditions. Therefore drug release from this dosage form was studied in 0.1N HCl for a period of 4 hours and the data compared with that in pH 6.8 phosphate buffer to prove pH independence.

TABLE 4

In-vitro drug release in different pH media

| Time (hrs) | Composition 1 (pH 6.8 buffer) % cum. rel. | Composition 1 (0.1N HCL) % cum. rel. |
|---|---|---|
| 0 | 0 | 0 |
| 1 | 15.5 | 17.2 |
| 2 | 21.2 | 23.4 |
| 4 | 33.19 | 30.55 |

Figure 2:
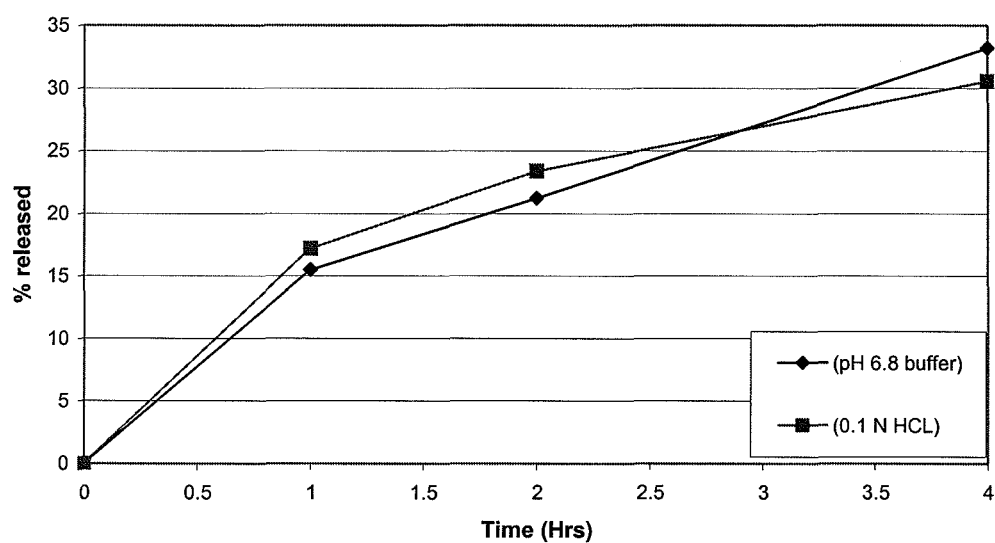
FIG. 2: In vitro release of composition 1 in different media.

No significant difference in the in vitro release profile was seen in the two media, indicating that the composition provides a pH independent in vitro drug release profile for a considerable period of time (FIG. 2).

Example 3

Preparation and the Drug Release Profile of the Sustained Release Tablet Dosage Form Comprising Individual Polymers

TABLE 5

Composition of the formulation

| Ingredients | Composition 2 (mg/tablet) | Composition 3 (mg/tablet) |
|---|---|---|
| Metoprolol succinate | 47.5 | 47.5 |
| Poly (methacrylic acid, methyl methacrylate) (EudragitL100 ®) | 150 | — |
| Copovidone (Kollidon VA 64) | 10 | 10 |
| Kolidon SR | — | 150 |
| Magnesium stearate | 2.5 | 2.5 |
| Water, Purified | q.s. | q.s. |

Procedure

Weighed quantities of metoprolol succinate and release retardant were granulated using a solution of Kolidon VA64 in purified water. The granules were mixed with balance quantity of release retardant and magnesium stearate and then compressed using a compression machine.

In vitro drug release was studied in 500 ml of pH 6.8 buffer using USP type II dissolution apparatus with 50 rpm rotation speed, the temperature being 37±1° C.

Table 6 shows the drug release profile of both composition 2 and 3

TABLE 6

In vitro drug release in pH 6.8 buffer

| Time (hours) | Composition 2 % Cumulative Drug Release | Composition 3 % Cumulative Drug Release | Marketed Product Cumulative Drug Release |
|---|---|---|---|
| 0 | 0 | 0 | 0 |
| 1 | 21.2 | 18.1 | 11.9 |
| 2 | 39.8 | 33.8 | 14.3 |
| 4 | 66.2 | 59.3 | 25.4 |
| 6 | 84.6 | 76.1 | 35.5 |
| 8 | 97.5 | 87.9 | 45.8 |

Figure 3:
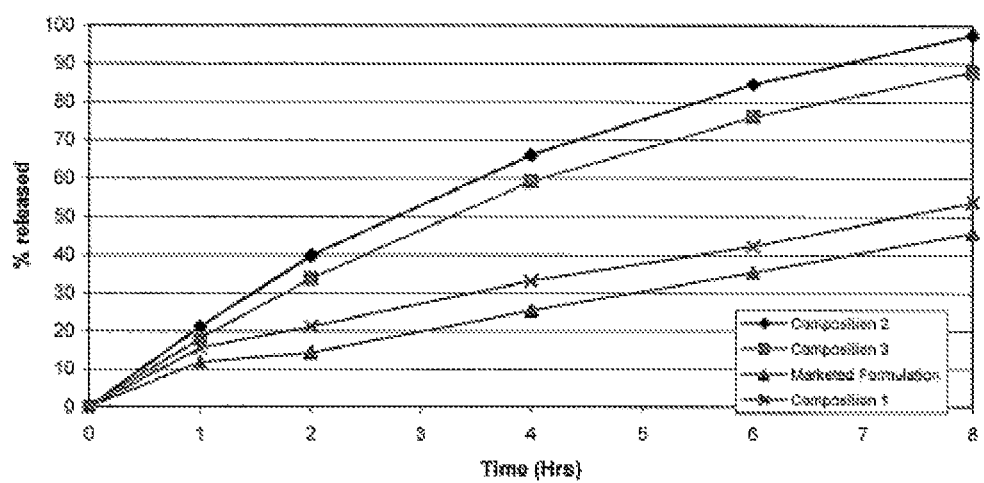
FIG. 3: Comparative in vitro release profile of composition 2, composition 3 and composition 1 with marketed formulation.

It is evident from the above examples and FIG. 3, that when both release retardants were employed alone, the resulting release profile was much faster than the marketed product as well as than the product having a combination of the two release retarding polymers (Composition 1).

Aforesaid results clearly establish the synergy existing in the combination of a non-swelling pH dependent release retarding polymer and a non-swelling pH independent release-retarding polymer.

Example 4

Preparation and the Drug Release Profile of the Sustained Release Tablet Dosage Form Coated with a Functional Coat

TABLE 7

Composition of the formulation

| Ingredients | Composition 4 (mg/tablet) |
|---|---|
| Metoprolol succinate | 190 |
| Poly (methacrylic acid, methyl methacrylate) (Eudragit L100 ®) | 160 |
| Copovidone (Kollidon VA 64) | 50 |
| Kollidon SR | 140 |
| Magnesium stearate | 10 |
| Hypromellose 5 cps | 44 |
| Ethyl cellulose aqueous dispersion | 11 |
| Glycerin | 4.4 |
| Water, Purified | q.s. |

Procedure

Weighed quantities of metoprolol succinate and Eudragit L100® were granulated using a solution of Kollidon VA 64 in water. The granules were mixed with Kollidon SR, Kollidon VA64 and magnesium stearate and then compressed. The tablets were further coated with a functional coat of ethyl cellulose and hypromellose.

In vitro drug release was studied in pH 6.8 buffer and pH change dissolution media (i.e. 0.01N HCl for 2 hrs followed by pH 6.8 buffer for 18 hrs) using USP type II dissolution apparatus with 50 rpm rotation speed temperature being 37±1° C.

Table 8 shows the drug release profile of composition 4 in pH 6.8 buffer and pH change media.

TABLE 8

In vitro drug release in pH 6.8 buffer and pH change media

| Time (hours) | % Cumulative Drug Release in pH 6.8 buffer | % Cumulative Drug Release in pH change media |
|---|---|---|
| 0 | 0 | 0 |
| 1 | 4.3 | 6.1 |
| 2 | 10.7 | 10.9 |
| 4 | 23.9 | 25.7 |
| 8 | 48.4 | 56.4 |
| 12 | 69.1 | 77.5 |
| 20 | 97.2 | 96.2 |

Figure 4:
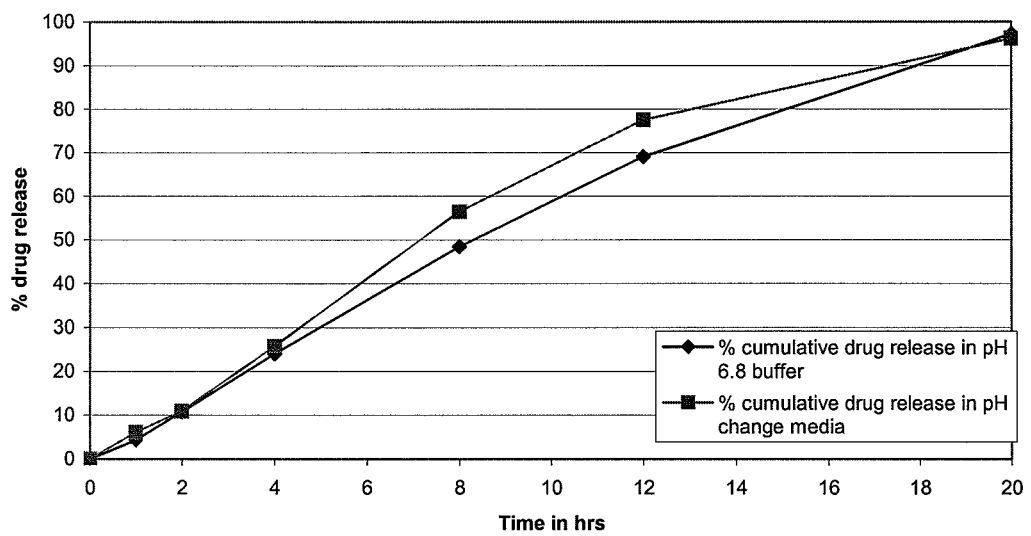
FIG. 4: Comparative in vitro release profile of composition 4 in different media

As evident from above table and FIG. 4, a pH independent release profile is achieved with composition 4.

Example 5

Preparation and the Drug Release Profile of the Sustained Release Tablet Dosage Form

TABLE 9

Composition of the formulation

| Ingredients | Composition 5 (mg/tablet) |
| --- | --- |
| Metformin HCl | 500 |
| Poly (methacrylic acid, methyl methacrylate) (Eudragit L100 ®) | 200 |
| Copovidone (Kollidon VA 64) | 16 |
| Kolidon SR | 400 |
| Microcrystalline cellulose | 72 |
| Magnesium stearate | 12 |
| Water, Purified | q.s. |

Procedure

Weighed quantities of metformin HCl and Eudragit L100® were granulated using solution of Kolidon VA64 in purified water. Granules were and mixed with Kolidon SR and Avicel PH 102. The blend was lubricated using magnesium stearate. The lubricated blend was compressed using capsule shaped punches.

In vitro drug release was studied in 900 ml pH 6.8 buffer using USP type I dissolution apparatus with 100 rpm rotation speed temperature being 37±1° C.

Table 10 shows the drug release profile of composition 5 in comparison with the commercial metformin HCl extended release tablet dosage form.

TABLE 10

In vitro drug release in pH 6.8 buffer

| Time (hours) | Composition 5 % Cumulative Drug Release | Marketed Formulation % Cumulative Drug Release |
| --- | --- | --- |
| 0 | 0 | 0 |
| 1 | 34.2 | 25.9 |
| 2 | 47.0 | 39.6 |
| 4 | 63.4 | 57.9 |
| 6 | 75.8 | 70.2 |
| 8 | 83.0 | 78.6 |
| 12 | 90.4 | 90.3 |

Figure 5:
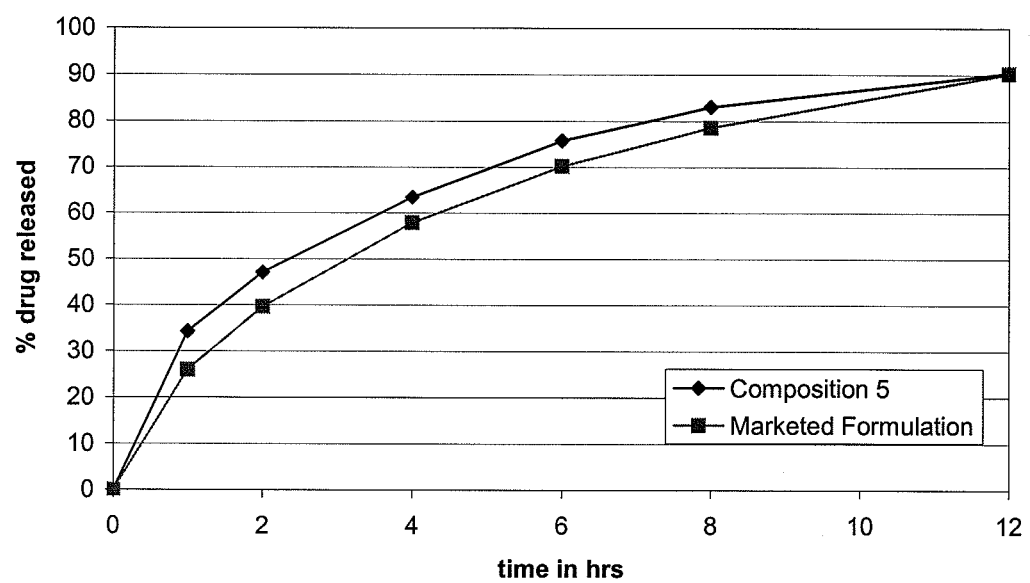
FIG. 5: Comparative in vitro release profile of composition 5 with marketed formulation.

As evident from above table and FIG. 5, composition 5 provides a drug release profile that is similar to that of the marketed formulation in pH 6.8 medium.

Example 6

Preparation and In Vitro Release Profile of Ascorbic Acid Sustained Release Tablet

TABLE 11

Composition of the formulation

| Ingredients | Composition 6 (mg/tablet) |
| --- | --- |
| Ascorbic acid | 500 |
| Poly (methacrylic acid, methyl methacrylate) (Eudragit L100 ®) | 250 |
| Copovidone (Kollidon VA 64) | 40 |
| Kollidon SR | 200 |
| Magnesium stearate | 10 |
| Water, Purified | q.s. |

Procedure

Weighed quantities of ascorbic acid, Eudragit L1000 and a part of Kollidon SR were granulated using solution of Kolidon VA64 in purified water. The granules were dried mixed with remaining quantity of Kolidon SR and Kollidon VA 64 and lubricated using magnesium stearate. The lubricated blend was compressed using oval punches. In vitro drug release was studied in 900 ml pH 6.8 buffer using USP type I dissolution apparatus with 100 rpm rotation speed temperature being 37±1° C.

Table 12 shows the drug release profile of composition 7 in pH 6.8 buffer.

TABLE 12

In vitro drug release in pH 6.8 buffer

| Time (hours) | Composition 6 % Cumulative Drug Release |
| --- | --- |
| 0 | 0 |
| 1 | 46.9 |
| 2 | 61.2 |
| 4 | 81.6 |
| 6 | 93.4 |
| 8 | 100.7 |

As evident from above table, it can be concluded that a combination of non swelling pH independent and non swelling pH dependent polymer can retard release of a high dose highly soluble drug ascorbic acid.

Example 7

Preparation of Phenylephrine Hydrochloride Sustained Release Tablet

TABLE 13

Composition of the formulation

| Ingredients | Composition 7 (mg/tablet) |
| --- | --- |
| Phenylephrine hydrochloride | 30 |
| Poly (methacrylic acid, methyl methacrylate) (Eudragit L100 ®) | 15 |
| MCC Avicel PH 102 | 93 |
| Kollidon SR | 60 |
| Magnesium stearate | 2 |

Procedure

Weighed quantities of phenylephrine hydrochloride, Eudragit L100, MCC Avicel PH 102, Kollidon SR and Magnesium stearate were mixed in a blender and then compressed into tablets.

The tablets of phenylephrine hydrochloride obtained showed good hardness and low friability.

Example 8

Preparation of Venlafaxine Hydrochloride Sustained Release Tablet

TABLE 14

Composition of the formulation

| Ingredients | Composition 8 (mg/tablet) |
|---|---|
| Venlafaxine hydrochloride | 84.86 |
| (equivalent to 75 mg Venlafaxine base) | |
| Hydroxy propylmethyl phthalate | 150.0 |
| Kollidon SR | 100.0 |
| Microcrystalline cellulose | 38.14 |
| Povidone QKollidon K30) | 20.0 |
| Magnesium stearate | 8.0 |
| Water, Purified | q.s. |

Procedure

Weighed quantities of Venlafaxine hydrochloride, Hydroxy propylmethyl phthalate, and Microcrystalline cellulose were mixed in a blender. The blend was granulated using solution of povidone in water. Granules were dried, sifted and lubricated using Kollidon SR and Magnesium stearate and compressed.

The tablets of venlafexine hydrochloride obtained showed good hardness and low friability.

Example 9

Preparation of Propranolol Hydrochloride Sustained Release Tablet

TABLE 15

Composition of the formulation

| Ingredients | Composition 9 (mg/tablet) |
|---|---|
| Propranolol hydrochloride | 120.0 |
| Eudragit S | 50.0 |
| Kollidon SR | 350.0 |
| Dicalcium phosphate | 70.0 |
| Starch 1500 | 30.0 |
| Aerosil | 6.0 |
| Talc | 6.0 |
| Water, Purified | q.s. |

Procedure

Weighed quantities of Propranolol hydrochloride, Eudragit S, Kollidon SR, Dicalcium phosphate and Starch 1500 were mixed in a blender. The mass was granulated using water, dried, sifted and lubricated using Aerosil and Talc and finally compressed into tablets.

The tablets of Propranolol hydrochloride exhibited desired performance characteristics.

Example 10

Preparation of Bupropion Hydrochloride Sustained Release Tablet

TABLE 16

Composition of the formulation

| Ingredients | Composition 10 (mg/tablet) |
|---|---|
| Bupropion hydrochloride | 150.0 |
| Eudragit L-100 | 150.0 |
| Compritol | 150.0 |
| Lactose | 75.0 |
| Magnesium stearate | 5.0 |

Procedure

Weighed quantities of Bupropion hydrochloride and Eudragit S were mixed in a blender. The mass was granulated using molten compritol. Granules of Bupropion thus obtained were further blended using Kollidon SR and lactose, lubricated using magnesium stearate and compressed into tablets.

The tablets of Bupropion hydrochloride exhibited desired physical and chemical characteristics.

Example 11

Preparation of Tramadol Hydrochloride Sustained Release Tablet

TABLE 17

Composition of the formulation

| Ingredients | Composition 11 (mg/tablet) |
|---|---|
| Tramadol hydrochloride | 200.0 |
| Hydroxy propylmethyl phthalate | 200.0 |
| Eudragit RS-PO | 150.0 |
| Silicified microcrystalline cellulose | 150.0 |
| Kollidon VA64 | 35.0 |
| Magnesium stearate | 8.0 |
| Water, Purified | q.s. |

Procedure

Weighed quantities of Tramadol hydrochloride, Hydroxy propylmethyl phthalate, Eudragit RS-PO and Silicified microcrystalline cellulose were mixed in a blender. The blend was then granulated using a solution of Kollidon VA64 in water. Granules were dried, sifted and lubricated using Magnesium stearate and compressed.

The tablets of Tramadol hydrochloride obtained showed good hardness and low friability.

Example 12

Preparation of Methylphenidate Sustained Release Tablet

TABLE 18

Composition of the formulation

| Ingredients | Composition 12 (mg/tablet) |
|---|---|
| Methylphenidate hydrochloride | 20.0 |
| Eudragit L100 | 50.0 |
| Lubritab | 100.0 |
| Microcrystalline cellulose | 25.0 |
| Magnesium stearate | 2.0 |
| Aerosil | 3.0 |

Procedure

Weighed quantities of methylphenidate hydrochloride, Eudragit L100, microcrystalline cellulose and Lubritab were mixed in a blender. The mass was heated to about 50° C. to carry out melt granulation. Mass was cooled and the resulting granules were lubricated using magnesium stearate and compressed into tablets.

The tablets of methylphenidate hydrochloride obtained, showed desired physical and chemical characteristics were obtained.

Example 13

Preparation of Ropinirole Hydrochloride Sustained Release Tablet

TABLE 19

Composition of the formulation

| Ingredients | Composition 13 (mg/tablet) |
|---|---|
| Ropinirole hydrochloride (equivalent to 3.0 mg base) | 3.42 |
| Eudragit L100 | 15.0 |
| Kollidon SR | 85.0 |
| Microcrystalline cellulose | 18.58 |
| Aerosil | 2.0 |
| Magnesium stearate | 1.0 |

Procedure

Weighed quantities of ropinirole hydrochloride, Eudragit L100, microcrystalline cellulose, Kollidon SR and Magnesium stearate were mixed in a blender and then compressed into tablets.

The tablets of ropinirole hydrochloride obtained showed good hardness and low friability.

Example 14

Preparation of Verapamil Hydrochloride Sustained Release Tablet

TABLE 20

Composition of the formulation

| Ingredients | Composition 14 (mg/tablet) |
|---|---|
| Verapamil hydrochloride | 240.0 |
| Eudragit L100 | 75.0 |
| Compritol | 75.0 |
| Kollidon SR | 320.0 |
| Lactose | 40.0 |
| Aerosil | 12.0 |
| Magnesium stearate | 6.0 |

Procedure

Weighed quantities of verapamil hydrochloride and Eudragit L100 were mixed in a blender. The mass was granulated using molten compritol. Granules of verapamil thus obtained were further blended using Kollidon SR and lactose, lubricated using magnesium stearate and compressed into tablets.

The tablets of verapamil hydrochloride obtained exhibited desired physical and chemical characteristics.

The invention claimed is:

1. A sustained release oral dosage form comprising:
   (a) a therapeutically effective amount of at least one pharmacologically active ingredient having aqueous solubility of greater than 1 mg/ml,
   (b) at least one non-swelling pH dependent release retardant, and
   (c) at least one non-swelling pH independent release-retardant; wherein the dosage form provides pH independent drug release for a considerable period of time after administration, and the dosage form is a matrix type dosage form.

2. The sustained release oral dosage form of claim 1, wherein said pharmacologically active ingredient is selected from class of anti-inflammatory, antipyretic, anticonvulsant and/or analgesic agents, tuberculostats, cardiocirculatory system drugs, antihistaminic agents, hypnotic sedatives, antineoplastic agents, bronchodilators, antiarrhythmic agents, surface anesthetics, antiepileptic, synthetic adrenocortical steroids, digestive system drugs, antibiotics, or combinations thereof.

3. The sustained release oral dosage form of claim 1, wherein said pharmacological active ingredient is selected from Neomycin Sulphate, Verapamil hydrochloride, Brimonidine tartrate, Morphine Sulphate, Lamivudine, Mepivacaine hydrochloride, Zidovudine, Lisinopril, Ropinirole hydrochloride, Abacavir sulphate, Pentoxifylline, valcyclovir hydrochloride, Daunorubicin, Ranitidine hydrochloride, Clonidine hydrochloride, Ondansetron hydrochloride, Diltiazem hydrochloride, Acyclovir Sodium, Albuterol Sulphate, Pravastatin Sodium, Didanosine, Atenolol, Stavudine, Mesalazine Sodium, Zanamirin, Doxycycline hyclate, Donepezil hydrochloride, Methyldopa, Timolol maleate, Naproxen, Naloxone hydrochloride, Alendronate sodium, Rizatriptan benzoate, Mecamylamine hydrochloride, Phenoxybenzamine hydrochloride, Captopril, Fluvastatin sodium, Benazepril hydrochloride, Pentosan polysulphate sodium, Levofloxacin, Cetirizine hydrochloride, Clidaymycin phosphate, Warfarin sodium, Propoxyphene hydrochloride, Potassium chloride, Pramipexole hydrochloride, Metoprolol succinate, Metoprolol tartrate, Metformin hydrochloride, Losartan potassium, Methyl phenidate hydrochloride, Montelukast sodium, Bisoprolol fumarate, Oxymorphoine hydrochloride, Amantadine hydrochloride, Sumatriptan succinate, Tramadol hydrochloride, Phenobarbital sodium, Cimetidine hydrochloride, Quinapril hydrochloride, Levomisole hydrochloride, Gabapentin, Ampicillin hydrochloride, Ceftrioxone sodium, Mepiridine hydrochloride, Guanidine hydrochloride, Venlafaxine hydrochloride, Propranolol hydrochloride, Promethazine hydrochloride, Bupropion hydrochloride, phenylephrine hydrochloride, ascorbic acid or combinations thereof.

4. The sustained release oral dosage form of claim 1, wherein said non-swelling pH dependent release retardant is selected from polymethacrylic acid derivatives, cellulose derivatives, acrylic acid derivatives, maleic acid copolymers, polyvinyl derivatives or mixtures thereof.

5. The sustained release oral dosage form of claim 1, wherein said non-swelling pH dependent release retardant is present in an amount from about 10 to about 90% by weight of the total composition.

6. The sustained release oral dosage form of claim 1, wherein said non-swelling pH independent, release retardant is selected from polyvinyl alcohol, polyvinyl acetate, a mixture of polyvinyl acetate (8 parts w/w) and polyvinylpyrrolidone (2 parts w/w), polymethacrylic acid derivatives, cellulose derivatives, waxes, lipids, fatty acids, fatty acid derivatives or combinations thereof.

7. The sustained release oral dosage form of claim 1, wherein said non-swelling pH independent release retardant is present in an amount from about 10 to about 90% by weight of the total composition.

8. The sustained release oral dosage form of claim 1 further comprising binder, lubricant, or diluent.

9. The sustained release dosage form of claim 1, wherein said dosage form is a tablet, capsule, pellet, granule, or powder.

10. The sustained release oral dosage form of claim 9, wherein said dosage form is prepared by wet granulation, direct compression, dry granulation or molding method.

11. The sustained release oral dosage form of claim 1, wherein said dosage form is coated.

12. The sustained release oral dosage form of claim 11, wherein said coated tablet comprises coat in the form of quick dissolving film of polymer selected from the group of hydroxypropylmethyl cellulose, hydroxypropyl cellulose, carboxymethyl cellulose, polyvinyl alcohol, poly methacrylate or mixtures thereof.

13. The sustained release oral dosage form of claim 11, wherein said coat is functional coat.

14. The sustained release oral dosage form of claim 13, wherein said functional coat comprises polymer selected from the group consisting of hydrophilic polymers, hydrophobic polymers, waxes or mixtures thereof.

15. The sustained release oral dosage form of claim 1, wherein said dosage form is multilayered tablet.

16. A method of administering a pharmaceutically active ingredient having aqueous solubility of greater than 1 mg/ml, the method comprising orally administering a sustained release oral dosage form comprising:
    (a) a therapeutically effective amount of at least one pharmacologically active ingredient having aqueous solubility of greater than 1 mg/ml,
    (b) at least one non-swelling pH dependent release retardant, and
    (c) at least one non-swelling pH independent, release-retardant; wherein the dosage form provides pH independent drug release for a considerable period of time after administration and the dosage form is a matrix type dosage form.

17. The sustained-release oral dosage form of claim 16, wherein said non-swelling pH dependent release retardant is present in an amount from about 10 to about 90% by weight of the total composition and said non-swelling pH independent release retardant is present in an amount from about 10 to about 90% by weight of the total composition.

18. The sustained release oral dosage form of claim 5, wherein said non-swelling pH independent release retardant is present in an amount from about 15% to about 75% by weight of the total composition.

19. The sustained release oral dosage form of claim 7, wherein said non-swelling pH dependent release retardant is present in an amount from about 15% to about 75% by weight of the total composition.

20. A sustained-release oral dosage form comprising,
    (a) a therapeutically effective amount of pharmacologically active ingredient having solubility of greater than 1 mg/ml,
    (b) non-swelling pH-dependent release retardant, and
    (c) ethyl cellulose;
wherein the dosage form provides a pH independent drug release for a considerable period of time after administration and the dosage form is a matrix type dosage form.

* * * * *